United States Patent
Marokkey

(10) Patent No.: US 8,828,748 B2
(45) Date of Patent: Sep. 9, 2014

(54) TEST STRUCTURES AND METHODS

(71) Applicant: Infineon Technologies AG, Neubiberg (DE)

(72) Inventor: Sajan Marokkey, Wappingers Falls, NY (US)

(73) Assignee: Infineon Technologies AG, Neubiberg (DE)

( * ) Notice: Subject to any disclaimer, the term of this patent is extended or adjusted under 35 U.S.C. 154(b) by 0 days.

(21) Appl. No.: 13/902,412

(22) Filed: May 24, 2013

(65) Prior Publication Data

US 2013/0258301 A1    Oct. 3, 2013

Related U.S. Application Data

(62) Division of application No. 12/792,406, filed on Jun. 2, 2010, now Pat. No. 8,450,122, which is a division of application No. 12/030,780, filed on Feb. 13, 2008, now Pat. No. 7,820,458.

(51) Int. Cl.

| | |
|---|---|
| *H01L 21/00* | (2006.01) |
| *H04R 31/00* | (2006.01) |
| *G01N 21/956* | (2006.01) |
| *H02N 99/00* | (2006.01) |
| *H04R 7/10* | (2006.01) |
| *H01J 37/26* | (2006.01) |

(52) U.S. Cl.
CPC ............. *H02N 99/00* (2013.01); *H04R 31/003* (2013.01); *G01N 21/956* (2013.01); *H04R 7/10* (2013.01); *H01J 37/26* (2013.01)
USPC .............................. 438/14; 438/311; 438/602

(58) Field of Classification Search
USPC ........................................... 438/14, 311, 602
See application file for complete search history.

(56) References Cited

U.S. PATENT DOCUMENTS

| 6,233,044 B1 | 5/2001 | Brueck et al. |
| 7,298,496 B2 | 11/2007 | Hill |
| 7,820,458 B2 * | 10/2010 | Marokkey ........................ 438/14 |
| 8,450,122 B2 * | 5/2013 | Marokkey ........................ 438/14 |
| 2007/0166650 A1 | 7/2007 | Wei |
| 2009/0091729 A1 | 4/2009 | Marokkey et al. |

(Continued)

OTHER PUBLICATIONS

Chou, W., et al., "Phase Errors in PSMs at the 90 nm Node," Semiconductor International, http://www.semiconductor.net/article/CA446614.html?industryid=3030&q=william+chou%2C+phase+shift, Sep. 1, 2004, pp. 1-7, Reed Business Information, Oak Brook, IL.

(Continued)

*Primary Examiner* — Laura Menz
(74) *Attorney, Agent, or Firm* — Slater & Matsil, L.L.P.

(57) ABSTRACT

Test structures and methods for semiconductor devices, lithography systems, and lithography processes are disclosed. In one embodiment, a method of manufacturing a semiconductor device includes using a lithography system to expose a layer of photosensitive material of a workpiece to energy through a lithography mask, the lithography mask including a plurality of first test patterns having a first phase shift and at least one plurality of second test patterns having at least one second phase shift. The layer of photosensitive material of the workpiece is developed, and features formed on the layer of photosensitive material from the plurality of first test patterns and the at least one plurality of second test patterns are measured to determine a optimal focus level or optimal dose of the lithography system for exposing the layer of photosensitive material of the workpiece.

12 Claims, 6 Drawing Sheets

(56) References Cited

U.S. PATENT DOCUMENTS

2009/0092926 A1    4/2009   Gutmann et al.
2009/0200546 A1*   8/2009   Marokkey .................. 257/48
2010/0239964 A1*   9/2010   Marokkey .................... 430/5
2010/0330469 A1*  12/2010   Marokkey .................... 430/5
2012/0208341 A1*   8/2012   Marokkey .................. 438/400
2013/0258301 A1*  10/2013   Dehe .......................... 355/55

OTHER PUBLICATIONS

Harper, C.A., "Electronic Materials and Processes Handbook," http://books.google.com/books?id= CQGPGwFuPRkC&pg=PT186&lpg=PT186&dq=gradient+refractive+index+doping+quartz&source=web&ots=4QQ0vGng-x&sig=4b-YyOGjX2+refractive+index+doping+D6kthlhP7qpUBYp$_{13}$  4, 2003, 2 pp., McGraw-Hill Professional, New York, NY.

* cited by examiner

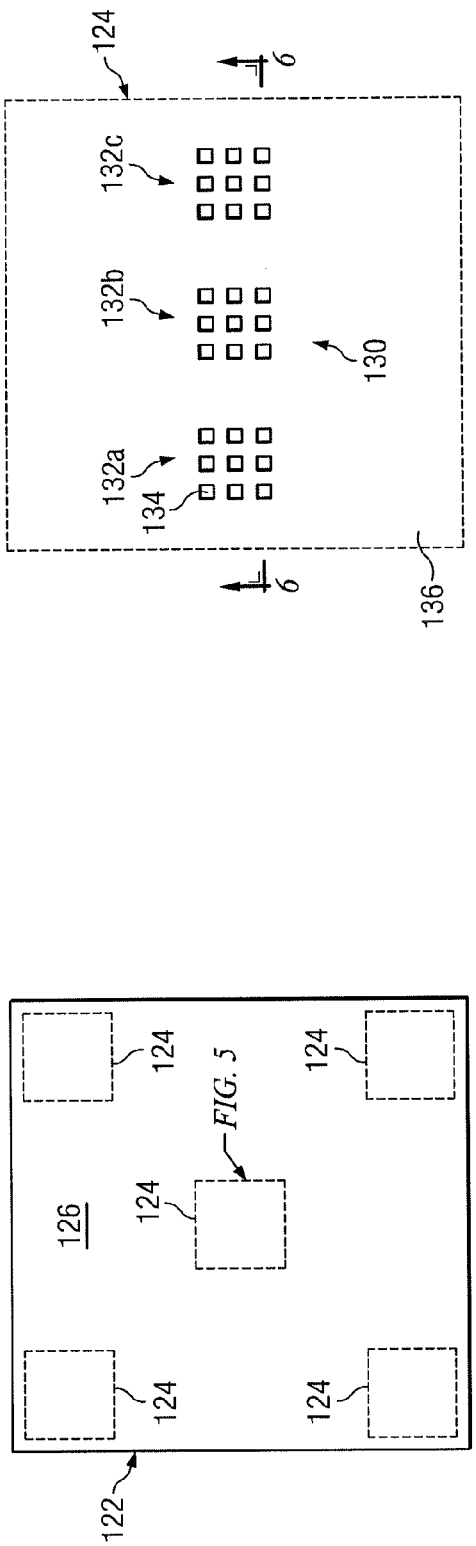
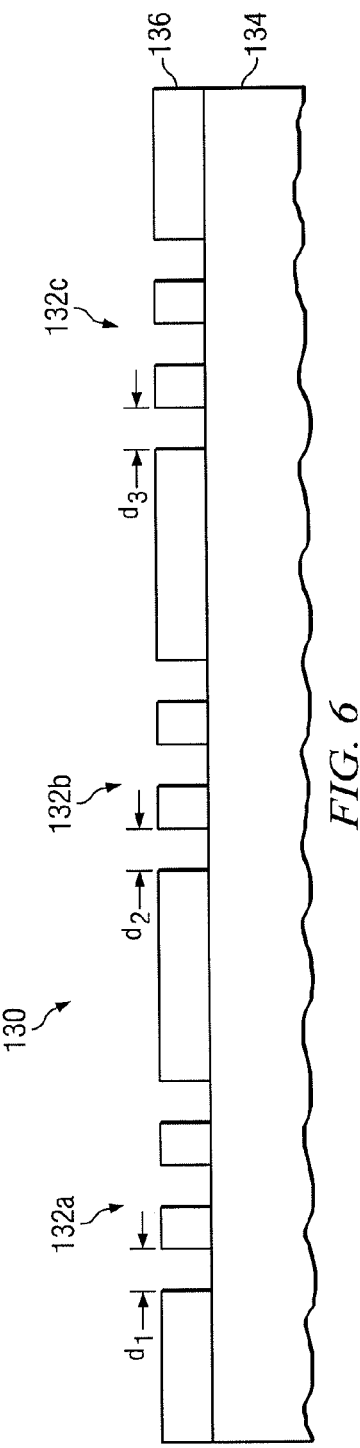
FIG. 4
FIG. 5
FIG. 6

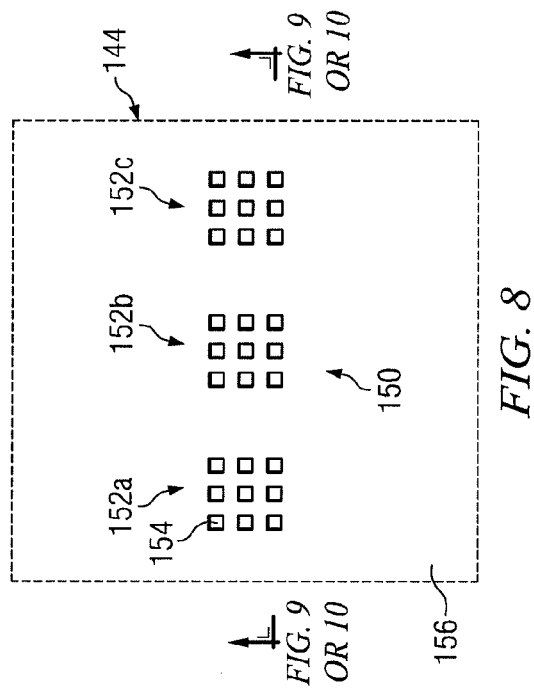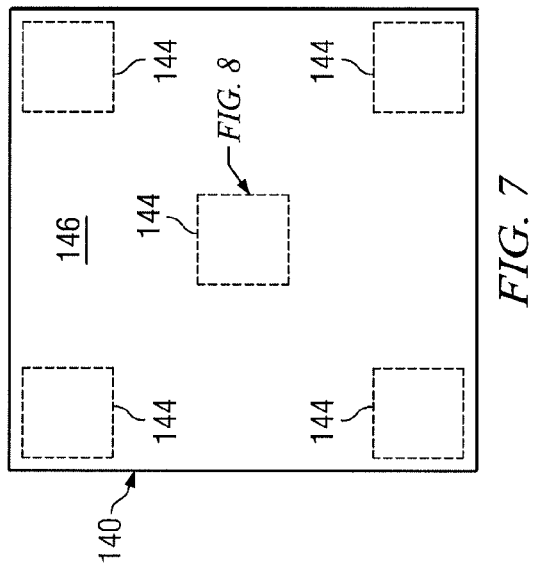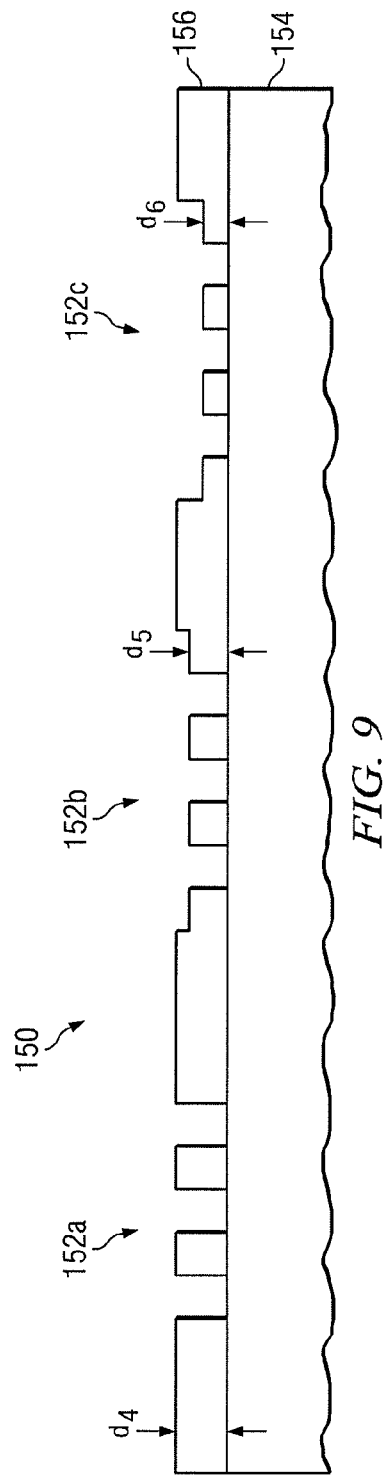

TEST STRUCTURES AND METHODS

This is a divisional application of U.S. application Ser. No. 12/792,406, entitled "Test Structures and Methods" which was filed on Jun. 2, 2010, which is a divisional application of U.S. application Ser. No. 12/030,780, entitled "Test Structures and Methods" which was filed on Feb. 13, 2008, now U.S. Pat. No. 7,820,458, and is incorporated herein by reference.

TECHNICAL FIELD

The present invention relates generally to the fabrication of semiconductor devices, and more particularly to test structures and methods for semiconductor devices, lithography systems, and lithography processes.

BACKGROUND

Semiconductor devices are used in a variety of electronic applications, such as personal computers, cell phones, digital cameras, and other electronic equipment, as examples. Semiconductor devices are typically fabricated by sequentially depositing insulating or dielectric layers, conductive layers, and semiconductive layers of material over a semiconductor substrate, and patterning the various material layers using lithography to form circuit components and elements thereon, forming an integrated circuit.

One type of semiconductor lithography involves positioning a patterned mask between a semiconductor workpiece and an energy source to expose portions of a photosensitive material deposited on the workpiece, transferring the mask pattern to the photosensitive material. The photosensitive material is then developed and used as a mask while exposed regions of a material on the workpiece are etched away. The photosensitive material is removed, and additional material layers are deposited and patterned in a similar fashion. There may be a dozen or more lithography mask levels required to manufacture an integrated circuit, for example.

Scanners are used in semiconductor device manufacturing to expose layers of photosensitive material. A portion, e.g., an exposure field, of a semiconductor workpiece is typically exposed at a time, and the scanner steps from one portion of the workpiece to the next, repeating the process until the entire workpiece is exposed.

As semiconductor devices are scaled down or reduced in size, lithography of semiconductor devices becomes more difficult. There are many parameters in a lithography system or process that may vary or shift, such as a focus level or exposure dose. The variations or shifts in these parameters may result in the formation of features on material layers of semiconductor devices that have undesired or unpredictable dimensions. Thus, it is desirable to detect variations of parameters such as focus level and dose in lithography systems or processes.

Therefore, what are needed in the art are improved methods and structures for testing lithography processes and systems, and test structures and methods for manufacturing semiconductor devices.

SUMMARY OF THE INVENTION

These and other problems are generally solved or circumvented, and technical advantages are generally achieved, by preferred embodiments of the present invention, which provide novel testing methods and structures for semiconductor devices.

In accordance with an embodiment of the present invention, a method of manufacturing a semiconductor device includes providing a workpiece having a layer of photosensitive material formed thereon. A lithography system is used to expose a layer of photosensitive material of a workpiece to energy through a lithography mask. The lithography mask includes a plurality of first test patterns having a first phase shift and at least one plurality of second test patterns having at least one second phase shift. The layer of photosensitive material of the workpiece is developed, and features formed on the layer of photosensitive material of the workpiece from the plurality of first test patterns and the at least one plurality of second test patterns are measured. An optimal focus level or an optimal dose of the lithography system for exposing the layer of photosensitive material of the workpiece is determined from the measurements of the features.

The foregoing has outlined rather broadly the features and technical advantages of embodiments of the present invention in order that the detailed description of the invention that follows may be better understood. Additional features and advantages of embodiments of the invention will be described hereinafter, which form the subject of the claims of the invention. It should be appreciated by those skilled in the art that the conception and specific embodiments disclosed may be readily utilized as a basis for modifying or designing other structures or processes for carrying out the same purposes of the present invention. It should also be realized by those skilled in the art that such equivalent constructions do not depart from the spirit and scope of the invention as set forth in the appended claims.

BRIEF DESCRIPTION OF THE DRAWINGS

For a more complete understanding of the present invention, and the advantages thereof, reference is now made to the following descriptions taken in conjunction with the accompanying drawings, in which:

FIG. 4 is a more detailed top view of an exposure field on the wafer shown in FIG. 3;

FIG. 5 shows a more detailed top view of a region of the exposure field of a semiconductor device shown in FIG. 4, illustrating a test structure comprising features that may be formed in each region of the exposure fields in accordance with embodiments of the present invention;

FIG. 6 shows a cross-sectional view of the exposure field of the semiconductor device shown in FIG. 5;

FIG. 7 shows a top view of a lithography mask comprising a substrate and an attenuating phase shifting material that may be used to pattern the exposure field shown in FIG. 4;

FIG. 8 shows a more detailed top view of a region 144 of the lithography mask 140 of FIG. 7;

FIG. 9 illustrates a cross-sectional view of an embodiment of the present invention wherein the thickness of the attenuated phase shifting material is varied in different regions of the mask to create different phase shifts;

Corresponding numerals and symbols in the different figures generally refer to corresponding parts unless otherwise indicated. The figures are drawn to clearly illustrate the relevant aspects of the preferred embodiments and are not necessarily drawn to scale.

DETAILED DESCRIPTION OF ILLUSTRATIVE EMBODIMENTS

The making and using of the presently preferred embodiments are discussed in detail below. It should be appreciated, however, that the present invention provides many applicable inventive concepts that can be embodied in a wide variety of specific contexts. The specific embodiments discussed are merely illustrative of specific ways to make and use the invention, and do not limit the scope of the invention.

Shrinking design rules in semiconductor devices require the use of higher numerical aperture lithography imaging systems, reducing the focus budget of lithography systems and processes considerably. In 45 nm and 32 nm minimum feature size technologies, for example, a focus budget of 0.15 µm has been proposed for various critical layers.

However, focus control of tools such as lithography systems and steppers is a challenge in the manufacturing environment of semiconductor devices. Conventional methods of determining focus include inline overlay measurement using grating patterns and scatterometry measurements. However, these methods require thorough characterization of the particular structures with reference to the particular photoresist process and photoresist stacks used. Thus, improved methods of determining focus levels of lithography systems and processes are needed in the art.

The present invention will be described with respect to preferred embodiments in a specific context, namely, in focus and dose detection, analysis, and feedback for lithography systems and processes of integrated circuits. Embodiments of the invention may also be applied, however, to other applications that would benefit from focus and dose detection and analysis, for example.

Embodiments of the present invention provide novel focus detection methods for lithography of material layers of semiconductor devices using attenuated phase shifting masks. The methods are adapted to detect focus deviations on semiconductor devices by measuring critical dimensions (CD) on novel test patterns, to be described further herein.

Figure 1:
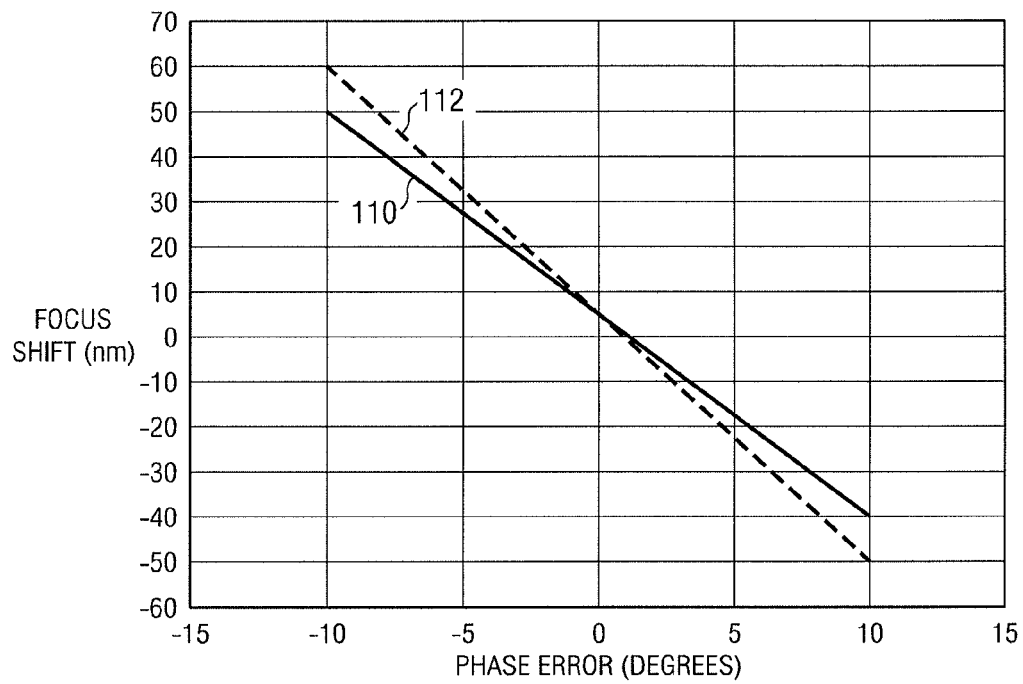
FIG. 1 is a graph illustrating an effect of phase error on best focus shift.

With reference now to FIG. 1, there is shown a graph illustrating the effect of phase error on best focus shift. The phase error in degrees is shown on the x axis, and the focus shift in nm is shown on the y axis, for measurements made of a 100 nm contact hole at 110 and of a 120 nm contact hole at 112. A phase variation on a lithography mask leads to a change in a best focus. For example, a change in phase by 10 degrees results in a change in the best focus by about 50 nm or greater, depending on the contact hole size, which can be seen by the graph in FIG. 1. The best focus variation slope vs. phase change is inversely proportional to the size of a contact hole.

The unintended effect of focus difference created by the phase of attenuated phase shifting material on a lithography mask illustrated in the graph of FIG. 1 is intentionally used in accordance with embodiments of the present invention to detect focus deviations, which may then be fed back in a process control system or may be used to make decisions on wafer lot disposition, to be described further herein.

Figure 2:
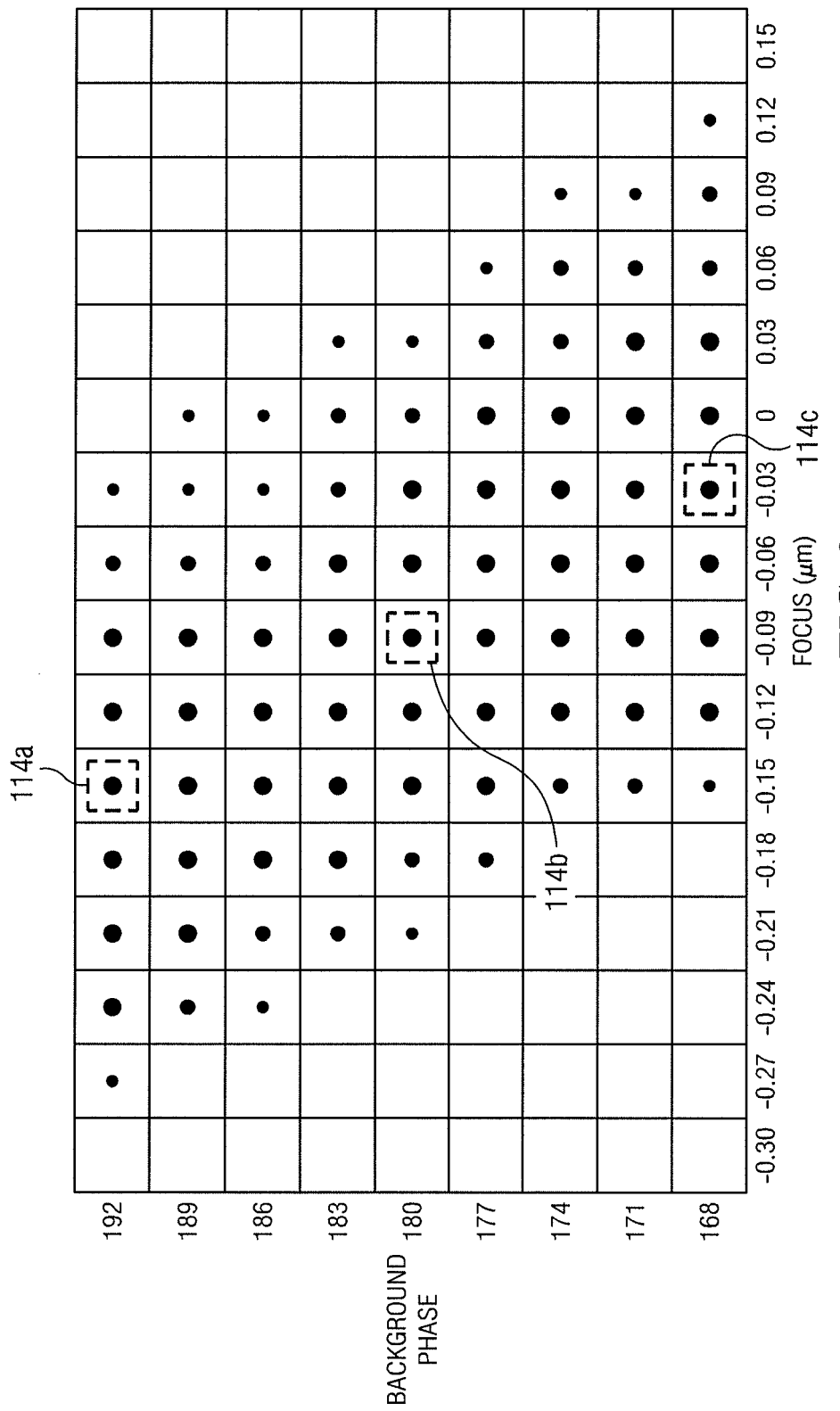
FIG. 2 is a plot of simulation results illustrating a shift in best focus versus background phase.

FIG. 2 is a plot of simulation results illustrating a shift in best focus versus background phase for 100 nm contact holes. Focus is shown in µm on the x axis, and background phase is shown in degrees on the y axis. The focus is plotted over a range of background phases with the best focus being shown in a central region of the plots of focus for each background phase. For example, the best focus is shown at 114a for a background phase of 192 degrees, the best focus is shown at 114b for a background phase of 180 degrees, and the best focus is shown at 114c for a background phase of 168 degrees. The focus for the background phases to the left and right of the best focus 114a, 114b, and 114c points on the plot becomes worse at points farther away from the best focus 114a, 114b, and 114c points, for example.

The unintended effect of a shift in best focus due to phase variations of attenuated phase shifting material on a lithography mask illustrated in the plot of FIG. 2 is intentionally used in accordance with embodiments of the present invention to detect focus and dose deviations and optimizations for a particular lithography system and process, which may be fed back in a process control system or may be used to make decisions on lot disposition, also to be described further herein.

In embodiments of the present invention, two or more test patterns having varying phase backgrounds are used to deduce focus deviation information from test features formed on a layer of photosensitive material of a semiconductor device using the test features. The test patterns comprise patterns for arrays of vias that have different phase shifts. The test patterns formed from the patterns for the arrays of vias are measured, and the test patterns comprise a particular critical dimension (CD) value that is a function of the focus setting. The measured CD values of the test patterns may be compared to each other and to a default or predetermined value to obtain focus information about a lithography system or process in accordance with embodiments of the present invention.

Figure 3:
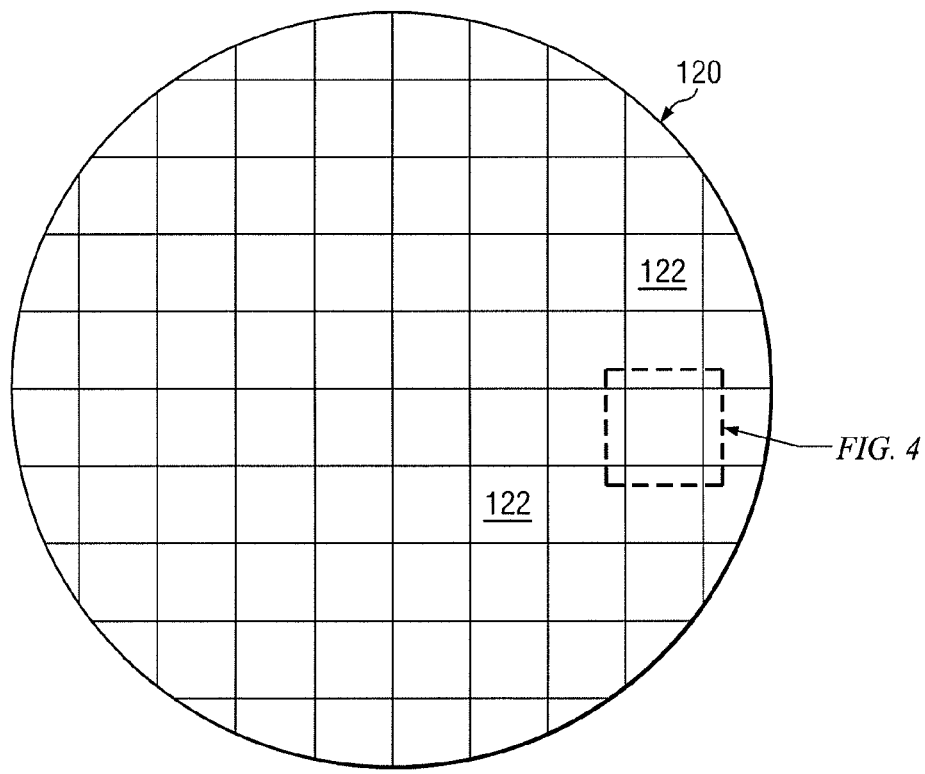
FIG. 3 shows a top view of a semiconductor wafer comprising a plurality of exposure fields in accordance with an embodiment of the present invention.

FIG. 3 shows a top view of a semiconductor wafer 120 comprising a plurality of exposure fields 122 in accordance with an embodiment of the present invention. The wafer 120 is generally round in a top view, and may include alignment features such as notches or straight edges, not shown. The exposure fields 122 across the surface of the wafer 120 may be square or rectangular, for example. The exposure fields 122 may comprise a pattern for a single die or integrated circuit, or alternatively, each exposure field 122 may comprise a pattern for several die or integrated circuits.

Each exposure field 122 comprises a region that is exposed in a single stepping process of a stepper, for example. The support for the wafer 120 in a lithography system (not shown) may be moved to position each exposure field 122 of the wafer 120 in order to transfer a pattern from a lithography mask (such as lithography mask 140 shown in FIG. 7) using energy through the mask 140 and a lens system of the lithography system onto a layer of photoresist (such as layer of photosensitive material 136 shown in FIGS. 5 and 6) on the wafer 120.

The wafer 120 is moved by the wafer support beneath the lens system from one exposure field 122 to another exposure field 122, moving through the rows and columns of the exposure fields 122 of the wafer 120 and exposing the exposure fields 122 until the entire wafer 120 is patterned, e.g., in an exposure process for production semiconductor devices, wherein the test features are formed on production semiconductor wafers 120. Alternatively, the test features of embodiments of the present invention may be formed on test wafers 120, wherein the test features may be formed only in some exposure fields 122 of the wafer 120, for example.

FIG. 4 is a more detailed top view of an exposure field 122 on the wafer 120 shown in FIG. 3. A top view of regions 124 that test patterns are formed in on a semiconductor device in the exposure field 122 in accordance with an embodiment of the present invention is shown. Test patterns may be formed in five regions 124 of an exposure field 122 in accordance with some embodiments of the present invention, as shown. The regions 124 comprising the test patterns are preferably located at the four corner regions and at the center region of the exposure field 122. The other regions 126 of the exposure field 122 may comprise areas where active or functioning circuitry of the semiconductor device is formed, for example. Regions 126 may comprise features for the active or functioning circuitry of a production semiconductor device, or alternatively, regions 126 may be unused, if the test features are formed in regions 124 on a test wafer 120.

FIG. 5 shows a more detailed top view of a region 124 shown in FIG. 4, illustrating a test structure 130 comprising features 132a, 132b, and 132c that may be formed in each region 124 of the exposure field 122 shown in FIG. 4 in accordance with embodiments of the present invention.

To form the test structure 130, a workpiece 134 is provided, as shown in the cross-sectional view of FIG. 6. The workpiece 134 may include a semiconductor substrate comprising silicon or other semiconductor materials covered by an insulating layer, for example. The workpiece 134 may also include other active components or circuits, not shown. The workpiece 134 may comprise a material layer to patterned disposed thereon, also not shown.

The workpiece 134 may comprise silicon oxide over single-crystal silicon, for example. The workpiece 134 may include other conductive layers or other semiconductor elements, e.g., transistors, diodes, etc. Compound semiconductors, GaAs, InP, Si/Ge, or SiC, as examples, may be used in place of silicon. The workpiece 134 may comprise a silicon-on-insulator (SOI) substrate. The workpiece 134 may comprise a test workpiece or a production workpiece, for example. The workpiece 134 may comprise a portion of a semiconductor wafer such as wafer 120 shown in FIG. 3.

Next, a layer of photosensitive material 136 is formed on the workpiece 134. The layer of photosensitive material 136 may comprise a photoresist such as a negative or positive photoresist, for example. An optional anti-reflective coating may be formed on the workpiece 134 before the layer of photosensitive material 136 is deposited, not shown.

The layer of photosensitive material 136 is patterned by providing a lithography mask such as mask 140 shown in FIGS. 7 through 10, to be described further herein. A lithography system is used to expose the layer of photosensitive material 136 over the workpiece 134 to energy (e.g., such as light or energy) through the lithography mask 140, and the layer of photosensitive material is developed to form a test structure 130 comprising features 132a, 132b, and 132c shown in FIGS. 5 and 6.

The features 132a, 132b, and 132c are also referred to herein as test features. The test features 132a, 132b, and 132c comprise a plurality of vias formed in the layer of photosensitive material 136. The test feature 132a is also referred to herein as a plurality of first test vias 132a, and the test feature 132b is also referred to herein as a plurality second test vias 132b. The test feature 132c is also referred to herein as a plurality of third test vias 132c.

In some embodiments, the test structure 130 only comprises two test features 132a, 132b, or 132c, for example. In other embodiments, the test structure 130 may comprise four or more test features 132a, 132b, or 132c, not shown. The test features 132a, 132b, and 132c may be formed proximate one another, as shown.

Each via of the test features 132a, 132b, and 132c comprises an aperture or hole formed in the layer of photosensitive material 136. The layer of photosensitive material 136 is disposed over the semiconductor workpiece 134 which may comprise a portion of a wafer 120 such as the one shown in FIG. 3, for example. The top surface of the workpiece 134 is visible from the top surface of the region 124 of the exposure field 122 within the vias of the test features 132a, 132b, and 132c, as shown.

In some embodiments, the plurality of first test vias 132a, the plurality of second test vias 132b, and the plurality of third test vias 132c of the test structure 130 each may comprise an array of three rows and columns of vias formed in the layer of photosensitive material 136, as shown in FIGS. 5 and 6. Alternatively, the test features 132a, 132b, and 132c of the test structure 130 may comprise other numbers of vias arranged in other sizes of arrays, e.g., comprising other numbers of columns and rows, not shown.

In some embodiments, the vias may comprise a minimum feature size or CD of a lithography system or process used to pattern the test features 132a, 132b, and 132c. Alternatively, the vias of the test features 132a, 132b, and 132c may comprise dimensions larger than a minimum feature size, for example. When measured, test features 132a may comprise a dimension $d_1$, test features 132b may comprise a dimension $d_2$, and test features 132c may comprise a dimension $d_3$. Although patterns on the lithography mask 140 may comprise the same dimension in all regions of the lithography mask 140, the dimensions $d_1$, $d_2$, and $d_3$ may vary for the test features 132a, 132b, and 132 due to focus or dose shifts, for example, which information may be used to determine information about possible focus or dose shifts of a lithography system or process in accordance with embodiments of the present invention.

Advantageously, an optimal focus level or an optimal dose of the lithography system or process used to pattern the test structure 130 may be determined from the test structure 130. For example, the optimal focus level or dose is determinable by measuring the plurality of first test vias 132a, the plurality of second test vias 132b, and the plurality of third test vias 132c, and comparing the measurements of the plurality of first test vias 132a, the plurality of second test vias 132b, and the plurality of third test vias 132c. The measurements of the dimensions $d_1$, $d_2$, and $d_3$ may also be compared to the measured dimensions or width of patterns in the lithography mask 140, for example.

FIG. 7 shows a top view of a lithography mask 140 that may be used to pattern the exposure field 122 shown in FIG. 4. The lithography mask 140 includes regions 144 that are used to pattern the regions 124 comprising the test structures 130 of the exposure field 122 shown in FIG. 5. Regions 146 of the lithography mask 140 are used to pattern regions 126 of the exposure field 122 shown in FIG. 4. The size of the lithography mask 140 corresponds to the size of the exposure field 122 patterned on the wafer 120. The lithography mask 140 may be larger than the exposure field 122 depending on the reduction factor of the lens system of the lithography system, for example, e.g., in a 2:1 or 4:1 reduction ratio system.

The lithography mask 140 may comprise a dedicated mask for testing semiconductor devices, for example. Alternatively, the lithography mask 140 may comprise patterns for patterning a material layer of a production or test semiconductor device, for example.

Figure 10:
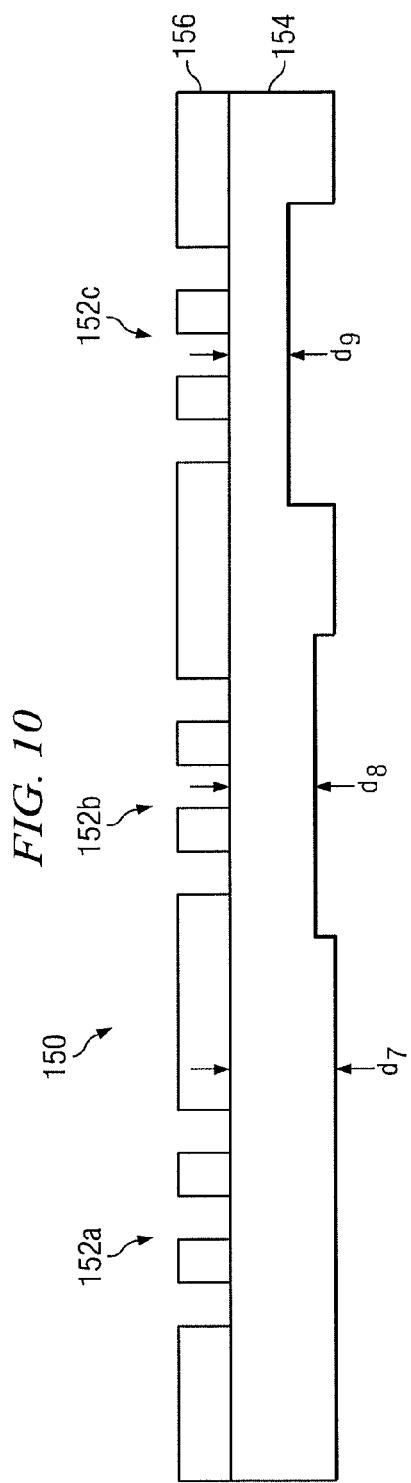
FIG. 10 illustrates a cross-sectional view of an embodiment of the present invention wherein the thickness of the substrate is varied in different regions of the mask to create different phase shifts.

FIG. 8 shows a more detailed top view of a region 144 of the lithography mask 140 of FIG. 7. FIGS. 9 and 10 show cross-sectional views of region 144 of the lithography mask 140 in accordance with embodiments of the present invention proximate the test structure pattern 150.

The lithography mask 140 includes a substrate 154 and an attenuated phase shifting material 156 disposed over the substrate 154. The substrate 154 may comprise a substantially transparent material, such as quartz or glass, and may comprise a thickness of about 500 μm, for example. Alternatively, the substrate 154 may comprise other dimensions.

The attenuated phase shifting material 156 may comprise a partially transmissive material such as MoSi, although other attenuating materials may also be used for the attenuated phase shifting material 156. The attenuated phase shifting material 156 may comprise a thickness of about 100 nm, or about 300 nm or less, as examples, although the attenuated phase shifting material 156 may alternatively comprise other dimensions.

The attenuated phase shifting material 156 comprises a test pattern 150 comprising a first test pattern in a first region 152a and at least one second test pattern in at least one second region 152b or 152c. The test pattern 150 comprises a pattern for the test structure 130 shown in FIG. 5. The first test pattern in the first region 152a comprises a pattern for the plurality of vias 132a shown in FIG. 5. The at least one second test pattern in the at least one second region 152b or 152c comprises a pattern for the plurality of vias 132b and/or 132c shown in FIG. 5. The patterns for the features in the first region 152a and the at least one second region 152b or 152c preferably comprise the same size or dimensions in some embodiments, for example. Alternatively, the patterns for the features in the first region 152a and the at least one second region 152b or 152c may comprise different sizes and dimensions.

The lithography mask 140 comprises a first phase shift in the first region 152a and at least one second phase shift in the at least one second region 152b or 152c, such that an optimal focus level or an optimal dose of a lithography system or process is determinable by measuring the test features 132a, 132b, and 132c formed on the photosensitive material 136 over the workpiece 134 or semiconductor device using the lithography mask 140. The phase shift in the first region 152a and the at least one second region 152b or 152c may be achieved by varying the thickness of the substrate 154, as shown in FIG. 10, by varying the thickness of the attenuated phase shifting material 156, as shown in FIG. 9, or by varying the thickness of both the substrate 154 and the attenuated phase shifting material 156.

Alternatively, the phase shift in the first region 152a and/or the at least one second region 152b or 152c of the lithography mask may be achieved by modifying the refractive index of the substrate 154 and/or the attenuated phase shifting material 156 proximate the patterns for the test features in the first region 152a and the at least one second region 152b or 152c. For example, the substrate 154 or the attenuated phase shifting material 156 of the lithography mask 140 may be implanted with ions or atoms of a substance, such as potassium, although other substances may also be used, to modify the optical characteristics of the mask 140 in the desired area. The attenuated phase shifting material 156 or the substrate 154, or both the attenuated phase shifting material 156 and the substrate 154 may include an implanted substance adapted to produce the first phase shift or the at least one second phase shift of the lithography mask 140, for example.

The phase shifts in regions 152a, 152b, or 152c are intentionally varied in accordance with embodiments of the present invention, to produce the test features 132a, 132b, and 132c such that measuring the CDs of the test features 132a, and 132b, and 132c provide focus and dose information of the lithography system and processes used to pattern the test features 132a, 132b, and 132c. After the manufacturing process for the lithography mask 140, for example, portions of the substrate 154 or attenuating phase shifting material 156 may be patterned and etched or implanted with a substance to create the phase shift variations in the various regions of the mask 140.

For example, in FIG. 9, an embodiment of the present invention is shown wherein the thickness of the attenuated phase shifting material 156 varies in regions 152a, 152b, and 152c. The thickness of the attenuated phase shifting material 156 in region 152a may comprise a dimension $d_4$ that is greater than the thickness of the attenuated phase shifting material 156 in region 152b comprising dimension $d_5$. The thickness of the attenuated phase shifting material 156 in region 152b may comprise a dimension $d_5$ that is greater than the thickness of the attenuated phase shifting material 156 in region 152c comprising dimension $d_6$. The dimensions $d_4$, $d_5$, and $d_6$ may vary by about 50 nm or less, or may vary by about 300 nm or less in some embodiments, for example, depending on the amount of phase shift desired.

The thicknesses of the attenuated phase shifting material 156 in regions 152a, 152b, or 152c may comprise dimensions $d_4$, $d_5$, and $d_6$ such that an amount of phase shift in the first region is about 180 degrees, and wherein the amount of phase shift in the at least one second region is about (180 degrees+x) or about (180 degrees−x), wherein x comprises a predetermined amount. The amount of phase shift in regions 152a, 152b, or 152c is also referred to herein as a background phase shift of the regions 152a, 152b, or 152c of the lithography mask 140.

The predetermined amount x of the variation of the phase shifts from about 180 degrees may comprise about 1 to 20 degrees, for example. In some embodiments, for example, the predetermined amount x comprises about 10 degrees. For example, in some embodiments, the phase shift in region 152b may comprise about 180 degrees, the phase shift in region 152a may comprise about 170 degrees, and the phase shift in region 152c may comprise about 190 degrees.

The first thickness comprising dimension $d_4$ and the at least one second thickness (e.g., comprising dimensions $d_5$ or $d_6$) of the attenuated phase shifting material 156 may be determined using Equation 1 in some embodiments:

$$T/PS = \frac{\lambda}{n*360}; \qquad \text{Eq. 1}$$

wherein T comprises the first thickness $d_4$ or the at least one second thickness $d_5$ or $d_6$, wherein PS is the amount of phase shift in the first region 152a or the at least one second region 152b or 152c in degrees, wherein $\lambda$ comprises a wavelength of an exposure process used to pattern a photosensitive material of a semiconductor device (e.g., the layer of photosensitive material 136 shown in FIGS. 5 and 6) using the lithography mask 140, and wherein n comprises a refractive index of the attenuated phase shifting material 156, for example.

In the embodiment shown in FIG. 9, varying the thickness of the attenuated phase shifting material 156 may result in a change in the transmissivity of the attenuated phase shifting material 156 in some regions 152a, 152b, or 152c. If the transmissivity of the attenuated phase shifting material 156 is sensitive to the via feature size printed, via size biasing in some regions 152a, 152b, or 152c may be used. For example, the size of the first test pattern or the at least one second test pattern may be altered to compensate for the altered transmissivity, so that the altered transmissivity of the attenuated phase shifting material 156 does not deleteriously affect the testing process for focus and/or dose of the lithography system or process. Thus, in these embodiments, the patterns for the features in the first region 152a and the at least one second region 152b or 152c may comprise different sizes and dimensions, for example.

The phase shifts in regions 152a, 152b, and 152c may also be created by varying the thickness of the substrate 154. For example, in FIG. 10, an embodiment of the present invention is shown wherein the thickness of the substrate 154 of the lithography mask 140 varies in regions 152a, 152b, and 152c. The thickness of the substrate 154 in region 152a may comprise a dimension $d_7$ that is greater than the thickness of the substrate 154 in region 152b comprising dimension $d_8$. The thickness of the substrate 154 in region 152b may comprise a dimension $d_8$ that is greater than the thickness of the substrate 154 in region 152c comprising dimension $d_9$. The dimensions $d_7$, $d_8$, and $d_9$ may vary by about 100 nm or less, or by about 500 nm or less in some embodiments, for example, depending on the amount of phase shift desired.

As in the embodiment shown in FIG. 9, the thicknesses of the substrate 154 in regions 152a, 152b, or 152c may comprise dimensions $d_7$, $d_8$, and $d_9$ such that an amount of phase shift in the first region is about 180 degrees, and wherein the amount of phase shift in the at least one second region is about (180 degrees+x) or about (180 degrees−x), wherein x is the predetermined amount.

To test a lithography system or lithography process, a lithography system is provided, a workpiece such as workpiece 134 having the layer of photosensitive material 136 formed thereon as shown in FIGS. 5 and 6 is provided, and a lithography mask 140 such as the lithography mask 140 shown in FIGS. 7 through 10 is provided. A lithography system is also provided that includes the lithography mask 140, a support for the workpiece 134, an energy source disposed proximate the lithography mask 140, and a lens system disposed between the lithography mask 140 and the support for the workpiece 134.

Using the lithography system, the layer of photosensitive material 136 of the workpiece 134 is exposed to energy through the lithography mask 140, and the layer of photosensitive material 136 of the workpiece 134 is developed. Features formed on the layer of photosensitive material from the pattern for the plurality of first vias and the pattern for the plurality of the second vias are measured, and an amount of focus level shift or an amount of dose shift of the lithography system is determined from the measurements made.

Figure 11:
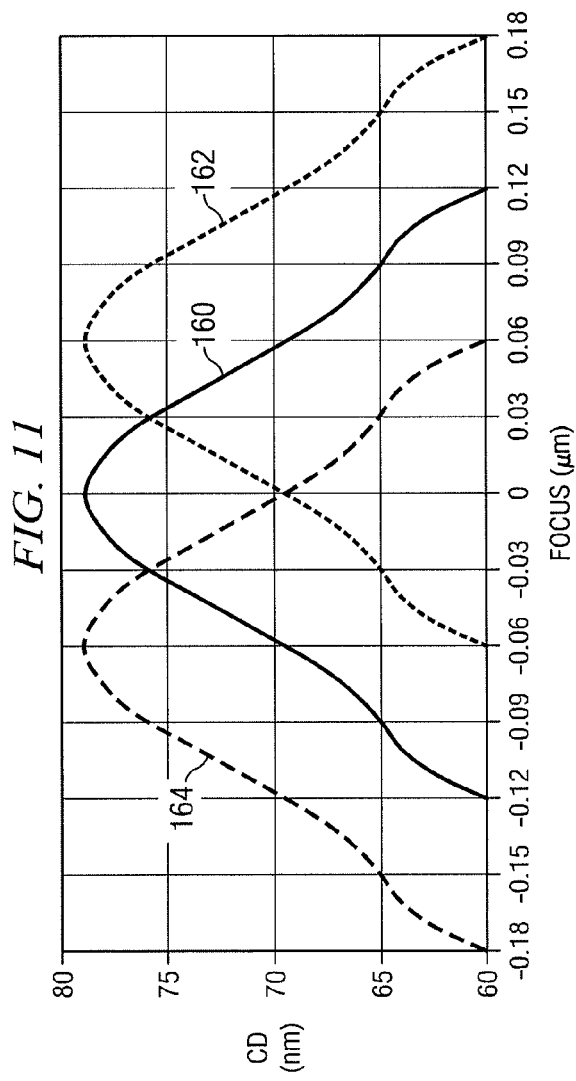
FIG. 11 shows a Bossung plot which illustrates effects of exposure dose and focus shifts.

For example, FIG. 11 shows a Bossung plot which illustrates effects of exposure dose and focus shifts. The focus level or value in μm is shown on the x axis and the measured CD is shown on the y axis. Measured dimensions of test features 132b formed by patterns with a phase shift of 180 degrees are shown at 160, measured dimensions of test features 132a formed by patterns with a phase shift of 190 degrees are shown at 164, and measured dimensions of test features 132c formed by patterns with a phase shift of 170 degrees are shown at 162.

The ideal or intended best focus for the lithography system or process is illustrated at 160 for a phase shift background of 180 degrees. The best focus for the graph 160 at 180 degrees is expected to be 78 nm, as can be seen in the peak of the graph 160 at a focus of 0. However, if the focus level shifts to the right, CDs measured in test features formed by patterns having a 170 degree phase shift increase, and CDs measured in test features formed by patterns having 180 and 190 degree phase shifts decrease. If the focus level shifts to the left, CDs measured in test features 132a, 132b, and 132c formed by patterns having a 190 degree phase shift increase, and CDs measured in test features 132a, 132b, and 132c formed by patterns having 180 and 170 degrees decrease. Thus, the magnitude and direction of a focus shift in the lithography system or process may be determined, based on measurements of the novel test features 132a, 132b, and 132c described herein.

If the test features 132a, 132b, and 132c formed in the three arrays of vias shown in FIG. 5 are formed using a mask 140 having three phase backgrounds of 170, 180, and 190 degrees, respectively, for example, there is a corresponding shift in best focus and the Bossung plot along the focus axis. By measuring the CDs of the test features 132a, 132b, and 132c at a set focus level, it is possible to separate the detection of dose changes from focus changes, and thus the dose/focus deviation is detected accurately, in accordance with embodiments of the present invention.

Embodiments of the present invention provide novel testing methods and structures that decouple focus shift from dose shift. For example, optimal dose and dose shift of the lithography system or process may also be determined using the novel test structures 150 described herein, for example. If the features measured on the layer of photosensitive material 136 vary by a similar amount for features formed from the plurality of first test patterns and features formed from the at least one plurality of second test patterns, then the optimal dose for the lithography system may be determined. After the optimal dose is determined, then the optimal dose information determined may be used to manufacture semiconductor devices 120.

As one example, the layer of photosensitive material 136 may comprise a first layer of photosensitive material, and exposing the first layer of photosensitive material 136 may comprise using a first dose. If the optimal dose determined is different than the first dose, then the first layer of photosensitive material 136 may be removed from the workpiece 134, a second layer of photosensitive material may be formed on the workpiece 134, and using the lithography system, the second layer of photosensitive material of the workpiece 134 may be exposed to energy through the lithography mask at a second dose, the second dose being substantially the same as the optimal dose determined. The second layer of photosensitive material may then be used to pattern a material layer of the semiconductor device 134.

As another example, referring again to the graph shown in FIG. 11, if the dose decreases, then all measured CDs of test patterns 132a, 132b, and 132c will decrease. If the dose increases, then all measured CDs of the test patterns 132a, 132b, and 132c will increase. Thus, the magnitude and direction of a dose shift in the lithography system or process may be determined, based on measurements of the novel test features 132a, 132b, and 132c described herein.

Figure 12:
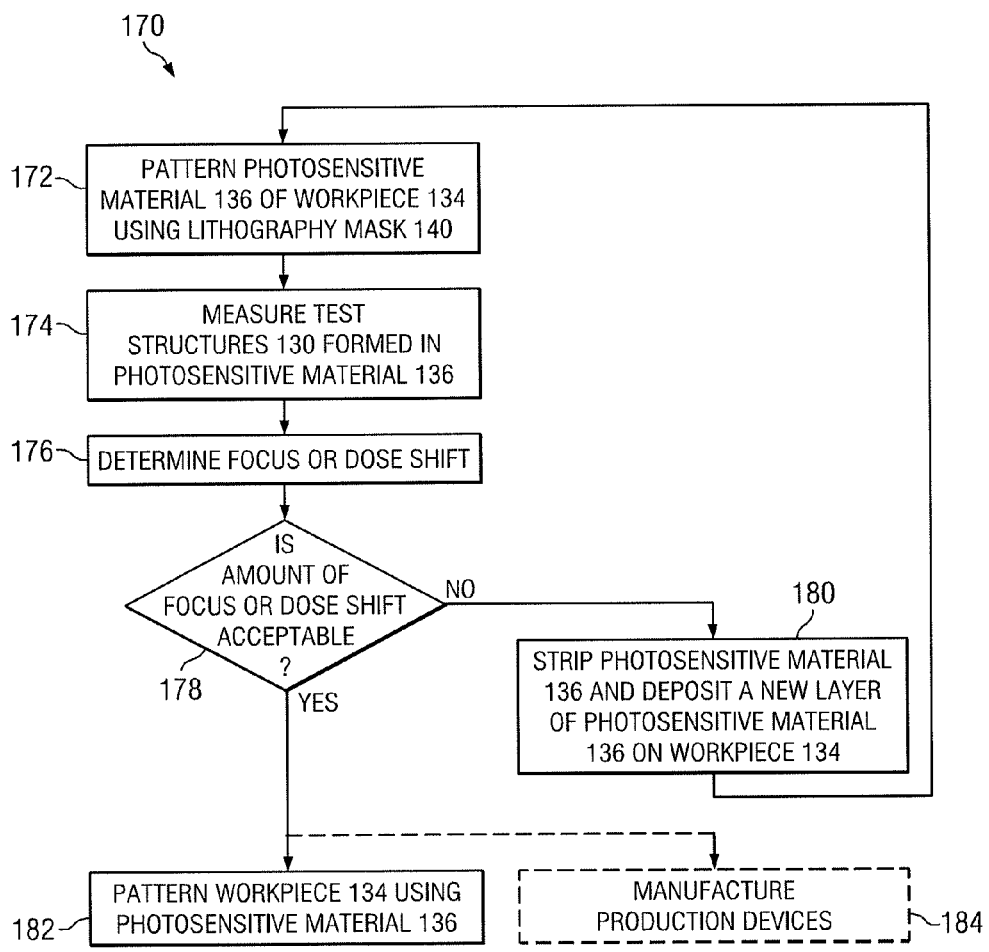
FIG. 12 shows a flow chart illustrating methods of manufacturing semiconductor devices in accordance with embodiments with the present invention.

Embodiments of the present invention also include methods of manufacturing semiconductor devices. For example, FIG. 12 shows a flow chart 170 illustrating methods of manufacturing semiconductor devices such as workpieces 134 in accordance with embodiments of the present invention. In step 172, a photosensitive material 136 of a workpiece 134 is patterned using a lithography mask 140 described herein. Test structures 130 formed in the photosensitive material 136 are measured (step 174), and focus shift and/or dose shift of the lithography system or process is determined (step 176).

The amount of focus shift and/or dose shift determined is compared to a threshold value of the focus shift or dose shift.

The threshold value of the focus shift or the dose shift may be established based on the particular lithography system or process, the particular amount of photosensitive material 136 being used, the type of semiconductor device 120 being manufactured, and other parameters of the lithography process, for example. If the amount of focus or dose shift determined is found to be acceptable (step 178), then the photosensitive material 136 may be used to pattern the workpiece 134 using the photosensitive material 136 (step 182), e.g., if other regions of the photosensitive material 136 have been patterned with active or functional circuitry for the workpiece 134. Alternatively, production semiconductor devices 120 may be manufactured (step 184, shown in phantom) if an acceptable amount of focus or dose shift is determined (step 178).

When the amount of focus shift and/or dose shift determined is compared to the threshold value of the focus shift or dose shift, if the amount of focus or dose shift determined is not acceptable (step 178), then the photosensitive material 136 may be stripped from the workpiece 134 and a new layer of photosensitive material 136 may be deposited on the workpiece 134 (step 180). A parameter of the lithography system may be altered, such as the focus or dose, and steps 172, 174, 176, and 178 may be repeated until an acceptable amount of focus or dose shift is found in the lithography system or process.

In other embodiments, features 132a, 132b, and 132c of the test structure 130 formed on the layer of photosensitive material 136 of the workpiece 134 from the plurality of first test patterns and the at least one plurality of second test patterns may be measured, and an optimal focus level or an optimal dose of the lithography system for exposing the layer of photosensitive material 136 of the workpiece 134 may be determined from the measurements of the features 132a, 132b, and 132c, for example. Exposing the layer of photosensitive material may comprise a first focus level, and if the optimal focus level is determined to be substantially the same as the first focus level, the layer of photosensitive material 136 may be used to pattern a material layer of the semiconductor device (e.g., the workpiece 134).

Embodiments of the present invention may be used on test workpieces 134 in some embodiments. For example, providing the workpiece 134 may comprise providing a test workpiece 134 having a first layer of photosensitive material 136 formed thereon. After the first layer of photosensitive material 136 is measured to determine the optimal focus level or optimal dose, a second workpiece 134 having a second layer of photoresist formed thereon is provided. The second layer of photoresist of the second workpiece 134 is patterned using the lithography system at the optimal focus level or optimal dose determined using the test workpiece 134. A plurality of second workpieces 134 may be patterned, e.g., in a production manufacturing run for semiconductor devices.

Other embodiments may be used to test semiconductor devices after developing the photosensitive material, and the novel testing methods described herein may be used to screen for unacceptable focus and dose shifts of the lithography system or process. For example, the layer of photosensitive material may comprise a first layer of photosensitive material, wherein exposing the first layer of photosensitive material comprises a first focus level. If the optimal focus level is determined to be different than the first focus level, a method of manufacturing a semiconductor device may further comprise removing the first layer of photosensitive material from the workpiece, forming a second layer of photosensitive material on the workpiece, and using the lithography system, exposing the second layer of photosensitive material of the workpiece to energy through the lithography mask at a second focus level, wherein the second focus level is substantially the same as the optimal focus level determined. The second layer of photosensitive material may then be used to pattern a material layer of the semiconductor device.

Advantageously, in-line metrology tools may be used for detecting focus and dose deviations in the methods described herein. Measuring the features 132a, 132b, and 132c formed on the layer of photosensitive material 136 may comprise measuring the features 132a, 132b, and 132c using a scanning electron microscope (SEM) or an optical microscope, for example, although alternatively, other instruments may be used.

The focus level or dose of the lithography system may be adjusted by the amount of the focus level shift or dose shift determined, in accordance with embodiments of the present invention. The focus level shift or dose shift may be used to calibrate or service the lithography system or process, for example.

The focus and dose deviations that are measurable and detectable using embodiments of the present invention may be used to make decisions on lot disposition or feedback in a process control system, as examples.

For example, in some embodiments, a method of testing a lithography system may include processing a plurality of workpieces comprising semiconductor wafers using the lithography system or process. The method may comprise periodically measuring features 132a, 132b, and 132c formed on the layer of photosensitive material 136 on the workpieces 134 from the pattern for the plurality of first vias and the pattern for the plurality of the second vias, and determining the amount of focus level shift or the amount of dose shift of the lithography system or process from the measurements made. The focus level or dose of the lithography system or process may then be altered based on the amount of focus level shift and amount of dose shift determined.

In some embodiments, e.g., during a manufacturing production run of a lot of wafers 120 or at other times, if the amount of the focus level shift or the amount of dose shift of the lithography system is determined to exceed the predetermined level of focus level shift or dose shift, an alarm of the lithography system or process may be activated, or manufacturing semiconductor wafers using the lithography system or process may be discontinued.

Embodiments of the present invention also include test structures 130 for semiconductor devices, as shown in FIGS. 5 and 6, and semiconductor devices 120 or 134 including the test structures 130. Embodiments of the present invention include lithography masks 140 including the novel test features, and lithography systems including and utilizing the lithography masks 140 described herein. Embodiments of the present invention also include methods of fabricating the novel lithography masks 140 described herein, for example.

Advantages of embodiment of the present invention include methods of detecting focus deviation, that may be implement in-line in a manufacturing process flow. The novel methods comprise using CD measurement, which provides a large amount of accuracy in the measurements because of the large degree of accuracy of CD measurement tools. The test structures 130 may be formed in test regions of semiconductors, proximate other types of test structures, for example.

The novel test structures and methods decouple focus shifts from dose shifts in a lithography system or process. The test structures and methods may be implemented in test wafers and masks, or in test regions of production wafers and masks.

For example, dedicated test masks including the novel test structures and methods described herein may be implemented on dedicated test wafers used to characterize lithography systems and tools. Or, the novel test structures and methods may be implemented on small test areas of production masks and wafers.

The novel test structures and methods described herein are advantageously easily implemented into existing process flows for manufacturing lithography masks and semiconductor devices.

Although embodiments of the present invention and their advantages have been described in detail, it should be understood that various changes, substitutions and alterations can be made herein without departing from the spirit and scope of the invention as defined by the appended claims. For example, it will be readily understood by those skilled in the art that many of the features, functions, processes, and materials described herein may be varied while remaining within the scope of the present invention. Moreover, the scope of the present application is not intended to be limited to the particular embodiments of the process, machine, manufacture, composition of matter, means, methods and steps described in the specification. As one of ordinary skill in the art will readily appreciate from the disclosure of the present invention, processes, machines, manufacture, compositions of matter, means, methods, or steps, presently existing or later to be developed, that perform substantially the same function or achieve substantially the same result as the corresponding embodiments described herein may be utilized according to the present invention. Accordingly, the appended claims are intended to include within their scope such processes, machines, manufacture, compositions of matter, means, methods, or steps.

What is claimed is:

1. A method of testing a lithography system comprising:
   (a) providing a workpiece having a layer of photosensitive material formed thereon;
   (b) providing a lithography mask comprising an attenuated phase shifting material comprising a pattern for a plurality of first vias in a first region and a pattern for a plurality of second vias in at least one second region, the first region having a first phase shift and the at least one second region having at least one second phase shift;
   (c) using the lithography system, exposing the layer of photosensitive material of the workpiece to energy through the lithography mask;
   (d) developing the layer of photosensitive material of the workpiece;
   (e) measuring features formed on the layer of photosensitive material from the pattern for the plurality of first vias and the pattern for the plurality of the second vias; and
   (f) determining an amount of focus level shift or an amount of dose shift of the lithography system from the measurements made.

2. The method of testing a lithography system according to claim 1, further comprising adjusting a focus level or a dose of the lithography system by the amount of focus level shift or dose shift determined, calibrating the lithography system using the amount of focus level shift or dose shift determined, or servicing the lithography system.

3. The method of testing a lithography system according to claim 1, wherein providing the lithography mask comprises providing a test lithography mask or a production lithography mask including patterns for integrated circuitry of the workpiece, or wherein providing the workpiece comprises providing a test workpiece or a production workpiece.

4. The method of testing a lithography system according to claim 1, further comprising processing a plurality of workpieces comprising semiconductor wafers using the lithography system, further comprising periodically:
   measuring features formed on the layer of photosensitive material on the workpieces from the pattern for the plurality of first vias and the pattern for the plurality of the second vias;
   determining the amount of focus level shift or the amount of dose shift of the lithography system from the measurements made; and
   altering a focus level or dose of the lithography system based on the amount of focus level shift and amount of dose shift determined.

5. The method of testing a lithography system according to claim 1, wherein measuring the features formed on the first layer of photosensitive material comprises measuring the features using a scanning electron microscope (SEM) or an optical microscope.

6. The method of testing a lithography system according to claim 1, further comprising:
   providing a predetermined level of focus level shift or dose shift;
   manufacturing a plurality of workpieces comprising semiconductor wafers using the lithography system;
   periodically measuring features formed on the layer of photosensitive material from the pattern for the plurality of first vias and the pattern for the plurality of the second vias; and
   determining the amount of focus level shift or the amount of dose shift of the lithography system from the measurements made, wherein if the amount of the focus level shift or the amount of dose shift of the lithography system is determined to exceed the predetermined level of focus level shift or dose shift, further comprising activating an alarm of the lithography system or discontinuing manufacturing the semiconductor wafers using the lithography system.

7. The method of testing a lithography system according to claim 1, wherein measuring the features formed on the layer of photosensitive material from the pattern for the plurality of first vias and the pattern for the plurality of second vias comprises measuring the critical dimensions (CDs) of the plurality of first vias and the critical dimensions (CDs) of the plurality of second vias.

8. The method of testing a lithography system according to claim 1, wherein determining the amount of focus level shift comprises measuring the CDs of the plurality of first vias and the plurality of second vias and applying a Bossung plot.

9. The method of testing a lithography system according to claim 1, wherein determining the amount of dose shift comprises determining a dose decrease if the pattern from the plurality of first vias and the pattern from the plurality of second vias decrease and determining a dose increase if the pattern from the plurality of first vias and the pattern from the plurality of second vias increase.

10. The method of testing a lithography system according to claim 1, further comprising, if the amount of the focus level shift or the amount of dose shift of the lithography system is determined to exceed a predetermined level of focus level shift or dose shift, removing the layer of photosensitive material on the workpiece.

11. The method of testing a lithography system according to claim 10, after removing the layer of photosensitive material, further comprising forming a new layer of photosensitive material on the workpiece and altering a focus level or dose of the lithography system based on the amount of focus level shift and amount of dose shift determined.

12. The method of testing a lithography system according to claim 11, after forming the new layer of photosensitive material, further comprising repeating steps (c)-(f).

\* \* \* \* \*